United States Patent [19]
Binkhorst

[11] 4,113,088

[45] Sep. 12, 1978

[54] STERILE PACKAGE

[76] Inventor: Richard D. Binkhorst, 125 E. 74th St., New York, N.Y. 10021

[21] Appl. No.: 803,959

[22] Filed: Jun. 6, 1977

[51] Int. Cl.² .................. B65D 81/18; A61F 1/16; A61F 1/24
[52] U.S. Cl. .................. 206/210; 3/13; 206/438; 206/45.34; 356/246; 422/292; 422/310
[58] Field of Search ............ 206/210, 205, 5.1, 316, 206/438, 45.33, 45.34, 303, 305; 3/13; 21/85, 105; 23/259; 356/246, 244

[56] References Cited

U.S. PATENT DOCUMENTS

| | | | |
|---|---|---|---|
| 3,093,242 | 6/1963 | Huyck et al. | 21/105 |
| 3,768,633 | 10/1973 | Nathan | 206/5.1 |
| 3,880,278 | 4/1975 | Brown | 206/205 |
| 3,994,027 | 11/1976 | Jensen et al. | 3/13 |

*Primary Examiner*—William T. Dixson, Jr.
*Attorney, Agent, or Firm*—Henry W. Foulds, Jr.

[57] ABSTRACT

A sterilizable package for intraocular lens implants is disclosed which is designed to permit optical inspection of the lens and measurement of the lens power under sterile conditions without removal from the sterile package.

7 Claims, 5 Drawing Figures

STERILE PACKAGE

This invention relates to packaging and in particular provides a package for an intraocular lens implant which permits the implant to be optically examined at any time before it is used without destroying the sterile package in which it is contained in order to ascertain that the implant has the desired power.

The required power of an intraocular lens implant can vary substantially depending upon a number of factors. [R. D. Binkhorst, Ophth. Surg. 6, (3) 17–31 (1975)]. While existing manufacturing techniques permit the careful determination of power in an intraocular lens implant, mistakes in packaging can and do occur. Consequently, it is highly desirable that the surgeon before using the implant be able to check the power of the lens while retaining the lens in sterile condition.

One solution of the problem has been to mark the packaging in which the lens is contained with the power in aqueous of the particular lens. The original determination of the lens power, however, had to have been made before it was packaged. Where a number of lenses are packaged, the possibility of confusion with package markings is always present, particularly as the lenses are extremely small. Typically, an intraocular lens implant (lens portion itself) is on the order of 4 millimeters diameter, while supports or loops for fixation, may extend the overall dimension to 9 or 10 millimeters. When handling several such small devices, the possibility of confusion always exists.

Another solution to the problem has been to mark the power of the lens on the lens itself. This solution, however, can lead to irritation after implantation, particularly since the only feasible way of marking the lens is by marring the surface of the lens. Moreover, this method is essentially subject to the same errors which can be made with package markings.

Ideally, the surgeon should be able to check the lens power before it is about to be implanted. The difficulty with this solution, however, lies in the fact that lenses are normally contained in sterile packages and checking the lens power by removing the lens from the package destroys its sterile condition.

It is, therefore, the principal object of this invention to provide a sterile package for an intraocular lens implant which is arranged in such manner that the power of the lens can be measured without removing the lens from the package and thus preserving its sterile condition.

In accordance with this invention, a sterile package for an intraocular lens implant is provided. The package has an outer sealed envelope of thin, optically transparent material which is suitable for ethylene oxide gas sterilization.

Within the package envelope, there is a case which retains the intraocular lens implant itself. The case desirably is made of a pair of separable cover parts which when closed form a space in which the lens can be positioned and which can be opened to remove the lens. Within one of the cover parts, a seat is formed which is shaped to receive the lens implant and the other cover part is designed to cooperate with the seat and retain the intraocular lens implant in position on the seat such that the position of the lens is relatively fixed. One of the cover parts is provided with an aperture which is aligned with the lens position such that the lens is visible through such aperture. The case is also provided with other apertures in both cover parts which are not aligned with the lens for the purpose of admitting ethylene oxide gas, or other sterilant, in order to effect the sterile condition of the lens implant.

The lens implant retained in the sterile package of this invention can be placed in a suitable optical measuring device for measuring the lens power. This is done by positioning the package with the aperture in the cover aligned in the field of vision of the optical measuring device. The lens is thus also in the field of vision of the measuring device. Preferably, the package envelope material is stretched tight so that it minimizes any interference with the optical measurement. Because the envelope is optically transparent, it causes no interference with measurement. The case, however, is normally of a heavier material and would interfere with the measurement except for the aperture which is aligned with the lens.

The typical optical measuring device for measuring lenses of the size of intraocular lens implants is the RADIUSCOPE which can be used to measure the radius of curvature of both surfaces of the lens from one side of the lens. Apertures, of course, can be provided in both cover parts aligned with the lens implant, if measurement from both sides is desirable.

For a more complete understanding of the practical application of this invention, reference is made to the appended drawings in which.

Figure 1:
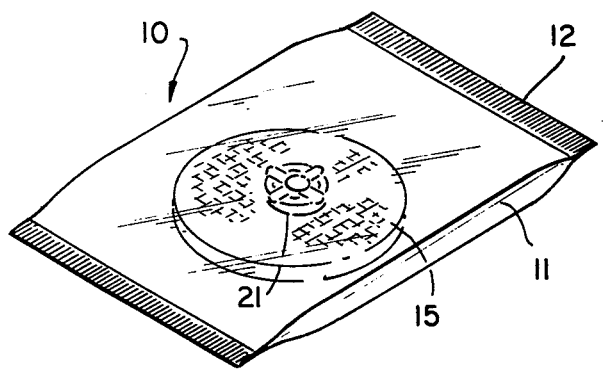
FIG. 1 is a perspective view of a sterile package in accordance with the present invention containing an intraocular lens implant.
Figure 2:
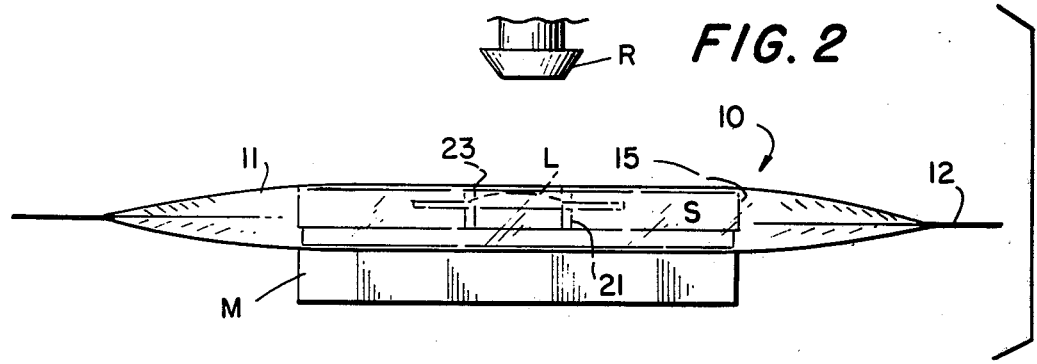
FIG. 2 is a view in elevation illustrating the positioning of the package in a device such as a RADIUSCOPE for measuring the lens power of the implant.

Referring particularly to FIGS. 1 and 2, the reference numeral 10 designates a sterile package in accordance with the present invention which includes an outer sealed envelope 11 formed of thin, optically transparent material. A case 15 is inserted in envelope 11 and the open end of envelope 11 indicated by the reference numeral 12 is sealed, for example, by heating where envelope 11 is made of thermoplastic material. The entire package is then sterilized with a gas such as ethylene oxide.

Figure 3:
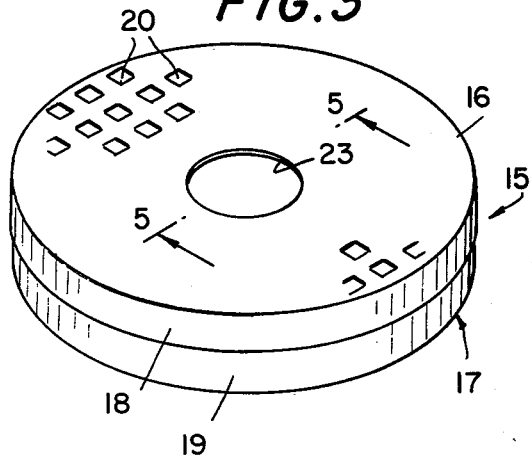
FIG. 3 is a perspective view of the case contained in the package shown in FIGS. 1 and 2.
Figure 4:
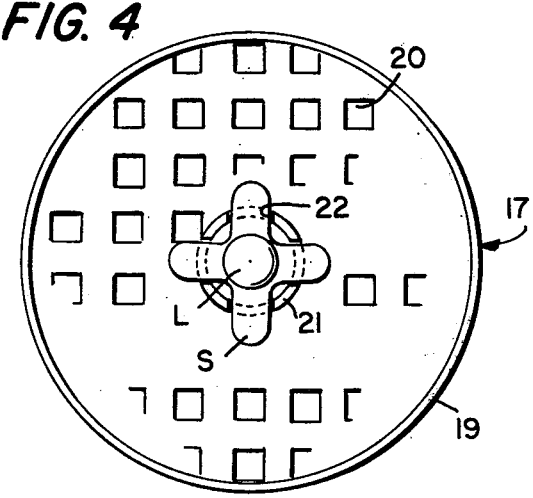
FIG. 4 is a plan view of one cover part of the case shown in FIG. 3 showing the seat and lens implant.
Figure 5:
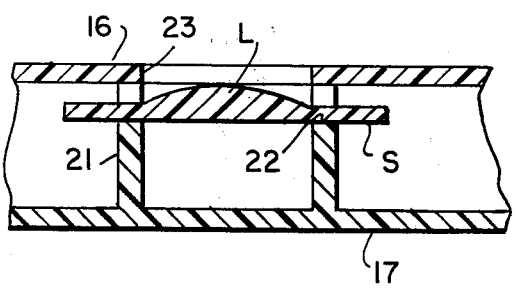
FIG. 5 is a cross-section taken at line 5—5 in FIG. 3.

Referring more particularly to FIGS. 3, 4 and 5, case 15 is flat and circular, being formed of two cover parts, 16 and 17, which can be hinged together but in the illustrated case, as shown in the drawings, are held together by frictional contact of an overlying flange 18 depending from cover part 16 and an underlying flange 19 upstanding from cover part 17. Cover parts 16 and 17 are preferably made from structurally strong plastic, for example, by injection molding. The preferred material of construction is polymethylmethacrylate, and the thickness of the cover parts should be sufficient to prevent damage to a lens implant retained in case 15 during normal handling. Both cover parts 16 and 17 are further provided with a series of apertures 20 in their circular faces which provide open communication between the interior and exterior of case 15 to permit a sterilant gas, such as ethylene oxide, in envelope 11 to enter case 15 freely.

Cover part 17 is further provided with a central tubular section 21 which is upstanding from the inner face of cover part 17 and which abuts the inner face of cover part 16 when cover parts 16 and 17 are positioned together in closed position. When cover part 16 is removed from cover part 17, the open end of tubular section 12 is exposed. This open end is provided in the illustrated case with four shallow notches 22 which are located at 90° intervals about section 21 and are sized to receive supports S on an intraocular lens implant L when the implant L is positioned against the open upper end of tubular section 21 with its lens portion in the center of the open end of section 21. Tubular section 21 thus functions as a seat for lens implant L and when cover part 16 is positioned against cover part 17 in the closed position, it functions to retain lens implant L in the seat formed by tubular section 21.

Cover part 16 is provided with a central aperture 23 in its circular face which is aligned with the open center of tubular section 22 of cover part 17 when the two cover parts are positioned together in closed position. Aperture 23 is thus also aligned with the lens portion of lens implant L and is of sufficient diameter to expose the entire lens portion of implant L.

As suggested above, the packaged implant L can be inspected by the surgeon prior to opening package 10, for example, just prior to implantation. This is accomplished utilizing the sealed package 10 with an optical measuring device, such as a RADIUSCOPE, capable of measuring contact lens power, for example, by measuring the radii of curvature of both surfaces of a lens. In FIG. 2, the reference numeral R designates the objective of the optical measuring device.

As can be seen in FIG. 2, the entire package 10 is positioned on lens mount M of the optical measuring device such that aperture 23 is aligned in the field of view of objective R. Preferably, as indicated above, the thin film of envelope 11 which overlies aperture 23 is stretched taut to minimize any interference with use of the optical measuring device in measuring the power of the lens portion of implant L which is thus positioned in the field of view of the optical measuring device and exposed to it through aperture 23. After checking that the power of implant L is correct, package 10 is then ready for use with implant L still in sterile condition. The use of the optical measuring device without the sterile package would have required resterilization of implant L before it could have been implanted.

It will also be apparent that while aperture 23 is shown in cover part 16, it could have been formed in cover part 17 at the lower end of tubular section 21 or similar apertures 23 could have been utilized in both cover parts. Because tubular section 21 functions as a seat for lens implant L, the preferred arrangement is that described, as lens implant L is held firmly in position when checking its power.

I claim:

1. A sterile package including an intraocular lens implant comprising a case having a pair of separable cover parts in closed position thereby enclosing a space therebetween, means in one said cover part forming a seat removably receiving said intraocular lens implant, said other cover part cooperating with said one cover part in said closed position to retain said intraocular lens implant in said seat forming means, means in a said cover part defining an aperture through said cover part aligned with said lens, and sealed package means of thin, optically transparent material enclosing said case.

2. A sterile package according to claim 1 treated with a sterilant gas.

3. A sterile package according to claim 2, in which said sterilant gas is ethylene oxide.

4. A sterile package according to claim 1 in which said cover parts are provided with a plurality of apertures permitting gaseous intercommunication between the interior and exterior of said case.

5. A sterile package according to claim 1 in which said aperture defining means is located in said other cover part.

6. A case having a pair of separable cover parts having a closed position enclosing a space therebetween, means in one said cover part forming a seat for removably receiving an intraocular lens implant, said other cover part cooperating with said one cover part in said closed position to retain a said intraocular lens implant in said seat forming means, and means in a said cover part defining an aperture through said cover part aligned with said seat forming means.

7. A case according to claim 6 in which said cover parts are provided with a plurality of apertures permitting gaseous intercommunication between the interior and exterior of said case.

* * * * *